(12) United States Patent
Boissonneault

(10) Patent No.: US 8,124,595 B2
(45) Date of Patent: Feb. 28, 2012

(54) GRADUATED ESTROGEN CONTRACEPTIVE

(75) Inventor: Roger M. Boissonneault, Long Valley, NJ (US)

(73) Assignee: Warner Chilcott Company, LLC, Fajardo, PR (US)

( * ) Notice: Subject to any disclaimer, the term of this patent is extended or adjusted under 35 U.S.C. 154(b) by 292 days.

(21) Appl. No.: 10/987,653

(22) Filed: Nov. 12, 2004

(65) Prior Publication Data

US 2005/0107351 A1 May 19, 2005

Related U.S. Application Data

(60) Provisional application No. 60/520,182, filed on Nov. 14, 2003.

(51) Int. Cl.
*A01N 45/00* (2006.01)
*A61K 31/56* (2006.01)

(52) U.S. Cl. ........ 514/169; 514/170; 514/171; 514/177; 514/182; 514/841; 514/843

(58) Field of Classification Search .................. 514/169, 514/170, 171, 177, 182, 841, 843
See application file for complete search history.

(56) References Cited

U.S. PATENT DOCUMENTS

| | | | | |
|---|---|---|---|---|
| 4,292,315 A | * | 9/1981 | Vorys | 514/178 |
| 4,921,843 A | | 5/1990 | Pasquale | 514/170 |
| 4,962,098 A | * | 10/1990 | Boissonneault | 514/170 |
| 5,552,394 A | * | 9/1996 | Hodgen | 514/178 |
| 5,888,543 A | | 3/1999 | Gast | 424/464 |
| 6,479,475 B1 | | 11/2002 | Gast | 514/170 |
| 6,511,970 B1 | | 1/2003 | Rodriguez | 514/170 |
| 7,569,560 B2 | * | 8/2009 | Boissonneault | 514/170 |
| 7,704,984 B2 | * | 4/2010 | Boissonneault | 514/170 |

FOREIGN PATENT DOCUMENTS

| | | |
|---|---|---|
| DE | 4313926 | 11/1994 |
| EP | 0253607 | 1/1988 |

OTHER PUBLICATIONS

U.S. Appl. No. 11/476,675, filed Jun. 2006, Boissonneault, Roger M.*
U.S. Appl. No. 12/534,902, filed Aug. 2009, Boissonneault, Roger M.*
U.S. Appl. No. 11/704,307, filed Feb. 2007, Ellman, Herman.*
Kaunitz, A.M.: "Efficacy, Cycle Control and Safety of Two Triphasic Oral Contraceptives" Contraception, vol. 61, pp. 295-302 (2000).

* cited by examiner

*Primary Examiner* — Johann Richter
*Assistant Examiner* — Mei-Ping Chui
(74) *Attorney, Agent, or Firm* — Fitzpatrick, Cella, Harper & Scinto

(57) ABSTRACT

A multiphasic estrogenic/progestogenic contraceptive regimen that provides for the reduction or elimination of estrogen in the initial phase is disclosed. Also described is a contraceptive kit that may be used to practice the method of the invention.

11 Claims, No Drawings

GRADUATED ESTROGEN CONTRACEPTIVE

This application claims the benefit of U.S. Provisional Patent Application No. 60/520,182, filed Nov. 14, 2003.

BACKGROUND OF THE INVENTION

1. Field of the Invention

This invention is directed to a method of contraception that provides for the reduction or elimination of estrogen in the initial phase of a multiphasic estrogenic/progestogenic contraceptive regimen without compromising contraceptive efficacy or cycle control. The invention is also directed to a multiphase contraceptive kit that may be used to practice the method of the invention.

2. Related Background Art

Contraceptive compositions containing both estrogenic and progestogenic compounds are well known. The progestogenic component of the composition is primarily responsible for the contraceptive efficacy of the composition, while the estrogenic component is employed to reduce undesired side effects, such as breakthrough bleeding or spotting.

The earliest of these estrogenic/progestogenic contraceptive compositions contained a relatively high level of estrogenic component. A constant goal, however, has been to reduce the estrogenic potency of such compositions without reducing contraceptive efficacy and increasing undesired side effects. As described in U.S. Pat. No. 5,888,543, in an attempt to achieve this goal, numerous regimens have been developed in which the progestin/estrogen combination is administered in a monophasic regimen (fixed dose) or as biphasic or triphasic regimens (varied dose).

A particularly advantageous technique for reducing total estrogenic administration is described in U.S. Pat. No. 4,962,098. This describes a triphasic method of contraception using a progestogen/estrogen combination in which the amount of estrogen is increased stepwise over the three phases. The first phase is 4-7 days, the second phase is 5-8 days and the third phase is 7-12 days. Preferably, the administration of the contraceptive compositions for the three phases will be 21 days followed by a 7 day placebo period. For all three phases the progesten is 0.5 to 1.5 mg of norethindrone acetate, while about 10 to 30 mcg of ethinyl estradiol is used in the first phase, about 20 to 40 mcg of ethinyl estradiol is used in the second phase and 30 to 50 mcg of ethinyl estradiol is employed in the third phase.

There is a continuing desire, however, to further reduce the amount of estrogenic component in an estrogenic/progestogenic composition with continued contraceptive efficacy while avoiding undesired side effects. Heretofore it was believed that at least 10 mcg of ethinyl estradiol or its estrogenic equivalent was needed in an estrogenic/progestogenic composition to assure contraceptive efficacy. It has now been surprisingly discovered that the amount of estrogenic component in the first phase of a triphasic regimen can be significantly reduced or eliminated without compromising efficacy or cycle control.

SUMMARY OF THE INVENTION

This invention is directed to a multiphasic method of contraception that provides for the reduction or elimination of administered ethinyl estradiol in the first phase without a reduction in contraceptive efficacy or an increase in undesired side effects. The method of this invention includes administering, in sequential steps, to a female of child bearing age the following compositions: (a) composition I for about 5 to about 9 days; (b) composition II for about 5 to about 9 days; and (c) composition III for about 8 to about 12 days. Compositions I, II and III all contain a progestogen in an amount equivalent to about 0.3 to about 1.5 mg, preferably about 0.5 to about 1.5 mg of norethindrone acetate. Composition I contains an estrogen in an amount equivalent to about 0 to less than about 10 mcg of ethinyl estradiol and both compositions II and III contain an estrogen in an amount equivalent to about 10 to about 50 mcg of ethinyl estradiol.

Significantly, the sequential administration of compositions I, II and III is repeated after a period of about 1 to about 4 days has elapsed after completion of the administration of composition III. Without being bound by theory, it is believed that this relatively short interim period between the sequential administration of the estrogenic/progestogenic components allows for the advantageous reduction or elimination of estrogen from the first phase of the above-described triphasic regimen without compromising efficacy or cycle control. It is also preferable that the amount of estrogen be increased by at least an amount equivalent to 5 mcg of ethinyl estradiol between composition II and composition III. In a preferred embodiment of this invention, the estrogen is ethinyl estradiol and the progestogen is norethindrone acetate.

Yet another embodiment of this invention is directed to a multiphase combination and contraceptive kit comprising a package containing daily dosages of: (a) a Phase I composition containing a progestogen in an amount equivalent to about 0.3 to about 1.5 mg, preferably about 0.5 to about 1.5 mg of norethindrone acetate and an estrogen in an amount equivalent to about 0 to about 10 mcg of ethinyl estradiol; (b) a Phase II composition containing a progestogen in an amount equivalent to about 0.3 to about 1.5 mg, preferably about 0.5 to about 1.5 mg of norethindrone acetate and an estrogen in an amount equivalent to about 10 to about 50 mcg of ethinyl estradiol; and (c) a Phase III composition containing a progestogen in an amount equivalent to about 0.3 to about 1.5 mg, preferably about 0.5 to about 1.5 mg of norethindrone acetate and an estrogen in an amount equivalent to about 10 to about 50 mcg of ethinyl estradiol; wherein the amount of estrogen in the Phase III composition is at least an amount equivalent to 5 mcg of ethinyl estradiol greater than the amount of estrogen in the Phase II composition. Preferably, the estrogen used in the kit is ethinyl estradiol and the progestogen is norethindrone acetate.

DETAILED DESCRIPTION OF THE INVENTION

The method of this invention is practiced by administration of the compositions in a numeric sequence with the Phase I composition being used first, the Phase II composition being used second, etc. If packaging and/or other requirements dictate, the method and kit described herein can be employed as part of a larger scheme for contraception or treatment of gynecological disorders. While the sequence in which Applicant's combinations are administered is important to their operation, it should be kept in mind that variations in timing and dosage can be tolerated when medical considerations so dictate.

Significantly, the method of this invention provides that the sequential administration of compositions I, II and III is repeated after a period of about 1 to about 4 days has elapsed after the completion of the administration of composition III. More preferably, the number of days between the completion of the administration of composition III and beginning the repeated sequential administration of compositions I, II and III is from about 2 to about 4 days. During this interim period an iron supplement and/or a placebo may be preferably administered on a daily basis, although there is no requirement for the administration of anything during this interim period, i.e., the period between the completion of the prior sequential administration of compositions I-III and the start of the next sequential administration of compositions I-III.

Estrogens which may be used in the present invention include, for example, ethinyl estradiol, 17β-estradiol, 17β-estradiol-3-acetate, mestranol, conjugated estrogens, USP and estrone or salts thereof. The amount of estrogen used is described herein as that which is "equivalent" in estrogenic potency to an amount of ethinyl estradiol. The equivalent estrogenic potency of an estrogen to ethinyl estradiol may be readily determined by one of ordinary skill in the art. It is contemplated that each Phase could employ one or more different estrogens that deliver a potency equivalent to the recited amount of ethinyl estradiol. It is also contemplated that the estrogen used in one Phase may be different than that used in another Phase. In a most preferred embodiment of this invention, however, the estrogen for each Phase, if present, is ethinyl estradiol.

Progestogens which may be used in the present invention include, for example, progesterone and its derivatives such as 17-hydroxy progesterone esters and 19-nor-17-hydroxy progesterone esters, 17-alpha-ethinyl testosterone, 17-alpha-ethinyl-19-nortestosterone (norethindrone) and derivatives thereof, norethindrone acetate, norgestrel, nogestamate, desogestrel and D-17-beta-acetoxy-17-beta-ethyl-17-alpha-ethinyl-gon-4-en-3-one oxime. Other exemplary progestogens include demegestone, drospirenone, dydrogesterone, gestodene, medrogestone, medroxy progesterone and esters thereof. The amount of progestogen used is described herein as that which is "equivalent" in progestogenic potency to an amount of norethindrone acetate. The equivalent progestogenic potency of a progestogen to norethindrone acetate may be readily determined by one of ordinary skill in the art. It is contemplated that each Phase could employ one or more different progestogens that deliver a potency equivalent to the recited amount of norethindrone acetate. It is also contemplated that the progestogen used in one Phase may be different than that used in another Phase. In a most preferred embodiment of this invention, however, the progestogen for each Phase is norethindrone acetate.

Accordingly, in a preferred embodiment of this invention the compositions employed in accordance with the invention will contain in Phase I about 0.3-1.5 mg, preferably about 0.5-1.5 mg norethindrone acetate and about 0 to less than about 10 mcg ethinyl estradiol, preferably about 0 to about 5 mcg ethinyl estradiol, in Phase II about 0.3-1.5 mg, preferably about 0.5-1.5 mg norethindrone acetate and about 10-50 mcg ethinyl estradiol, preferably about 20-40 mcg ethinyl estradiol, and in Phase III about 0.3-1.5 mg, preferably about 0.5-1.5 mg norethindrone acetate and about 10-50 mcg ethinyl estradiol, preferably about 25-50 mcg ethinyl estradiol, wherein the amount of ethinyl estradiol is increased by at least 5 mcg from Phase II to Phase III A significant aspect of the method and kit of this invention is that the Phase I composition has a significantly lower concentration of estrogen equivalent to ethinyl estradiol than previously considered possible, while maintaining contraceptive efficacy and avoiding or minimizing unwanted side effects such as break through bleeding. In one particularly preferred embodiment the amount of estrogen equivalent to ethinyl estradiol in the Phase I composition is about 5 mcg. In another particularly preferred embodiment the Phase I composition is substantially free of estrogen, and most preferably is substantially free of ethinyl estradiol. As used herein "substantially free" means that estrogen is not detectable or only pharmacologically insignificant minor levels are present.

An optional Phase IV composition, which contains an iron supplement, e.g., ferrous fumarate, and/or one or more placebos, can be used in conjunction with the other three.

The particularly preferred compositions employed in accordance with the invention in Phases I through IV will more preferably have the administration times and drug contents set forth in the following tables when a four-phase system is used. Each table sets forth relevant values for one of Applicant's preferred embodiments, or configurations, for administration of the system to females.

TABLE 1

| Phase | Days | mg Norethindrone acetate | mcg EE | mg Fumarate |
|---|---|---|---|---|
| I | 7 | 1.0 | 5 | 0 |
| II | 7 | 1.0 | 30 | 0 |
| III | 10 | 1.0 | 35 | 0 |
| IV | 4 | — | — | 75 |

TABLE 2

| Phase | Days | mg Norethindrone acetate | mcg EE | mg Fumarate |
|---|---|---|---|---|
| I | 7 | 1.0 | 0 | 0 |
| II | 7 | 1.0 | 30 | 0 |
| III | 10 | 1.0 | 35 | 0 |
| IV | 4 | — | — | 75 |

The norethindrone acetate (NA) and ethinyl estradiol (EE) are well known and readily available. Clearly, the amount of NA and EE may be varied in accordance with the disclosure of this invention. For example, the amount of NA set forth in Tables 1 and 2 could readily be adjusted from 1 mg to 0.5 mg or 0.4 mg.

The designation "mcg" refers to micrograms and "mg" to milligrams.

It should be noted that these tables are presented for illustrative purposes only. The substitution of functionally equivalent amounts and kinds of reagent(s) in these schemes is contemplated. For example, the use of sugar or other placebo in place of all or part of the ferrous fumarate is envisioned.

The compositions used in this invention are administered using a suitable daily dosage form. Tablets, pills, capsules and caplets are exemplary dosage forms.

In addition, the use of other conventional additives, e.g., fillers, colorants, polymeric binders, and the like is also contemplated. In general any pharmaceutically-acceptable additive which does not interfere with the function of the active components can be used in one or more of the compositions.

Suitable carriers with which the compositions can be administered include lactose, starch, cellulose derivatives and the like used in suitable amounts. Lactose is a preferred carrier. Mixtures of carriers, e.g. lactose, microcrystalline cellulose and starch, are operable.

While the norethindrone acetate is preferred, as previously noted it may be replaced by a different progestogen. Similarly, while the ethinyl estradiol component is preferred it may be completely or partially replaced with one or more conventional estrogenic substances, e.g., mestranol.

While the invention is discussed as potentially one employing four phases, it clearly may employ only three. Phase IV is not essential to the operation of the other three distinct phases. Thus a method or kit which does not contain the Phase IV component is operable and, in fact, will be preferred when suitable factors, e.g., economy, dictate the non-use of the Phase IV component. As previously noted, whether a Phase IV component is used or not, it is preferably that the period between the completion of the Phase III composition and the start of the Phase I composition in the subsequent sequence not exceed about 4 days.

The terms "method" and "kit" are used herein to encompass any drug delivery systems via the use of which the 3- or 4-phase scheme outlined above can be effectively administered to human females. Combinations of various dosage forms are operable.

A unique dosage pattern, i.e., a unique sequence of administration of a novel estrogen/progestogen combination has been discovered which minimizes the administration of estrogen in the first phase of a multiphase regimen, while also minimizing certain side effects, notably breakthrough bleeding, commonly associated with conventional low dosage pills.

Reasonable variations, such as those which would occur to a skilled artisan, can be made herein without departing from the scope of the invention.

What is claimed:

1. A method of contraception comprising the steps of sequentially administering to a female of child bearing age:
   (a) a composition I containing a progestogen in an amount equivalent to about 0.3 to about 1.5 mg norethindrone acetate and an estrogen in an amount equivalent to about 0.5 to about 5 mcg of ethinyl estradiol for about 5 to about 9 days;
   (b) a composition II containing a progestogen in an amount equivalent to about 0.3 to about 1.5 mg of norethindrone acetate and an estrogen in an amount equivalent to about 10 to about 50 mcg of ethinyl estradiol for about 5 to about 9 days;
   (c) a composition III containing a progestogen in an amount equivalent to about 0.3 to about 1.5 mg of norethindrone acetate and an estrogen in an amount equivalent to about 25 to about 50 mcg of ethinyl estradiol for about 8 to about 12 days; and
   (d) a composition IV which contains ferrous fumarate or is a placebo for 1 to 4 days, wherein the sequential administration of compositions I, II, III and IV is repeated upon the completion of the administration of composition IV and the daily administration of compositions I, II, III and IV is for a 28 day period and wherein the amount of estrogen in composition III is greater than the amount of estrogen in composition II by at least an amount equivalent to 5 mcg of ethinyl estradiol.

2. The method according to claim 1, wherein the progestogen in each composition is norethindrone acetate.

3. The method according to claim 1, wherein the estrogen in each composition is ethinyl estradiol.

4. The method according to claim 3, wherein composition I contains an amount of ethinyl estradiol from about 0.5 to about 5 mcg.

5. The method according to claim 4, wherein composition I contains about 5 mcg of ethinyl estradiol.

6. The method according to claim 1, wherein each of compositions I, II and III contain a progestogen in an amount equivalent to about 0.5 to about 1.5 mg of norethindrone acetate.

7. The method according to claim 1, wherein composition I contains about 1.0 mg of norethindrone acetate and is administered for about 7 days, composition II contains about 1.0 mg of norethindrone acetate and is administered for about 7 days, composition III contains about 1.0 mg of norethindrone acetate and is administered for about 10 days, and composition IV contains about 75 mg of ferrous fumarate and is administered for 4 days.

8. The method according to claim 7, wherein composition I contains about 5 mcg of ethinyl estradiol, composition II contains about 30 mcg of ethinyl estradiol and composition III contains about 35 mcg of ethinyl estradiol.

9. A method of contraception comprising the steps of sequentially administering to a female of child bearing age:
   (a) a composition I containing about 0.3 to about 1.5 mg norethindrone acetate and about 0.5 to about 5 mcg of ethinyl estradiol for about 5 to about 9 days;
   (b) a composition II containing about 0.3 to about 1.5 mg norethindrone acetate and about 10 to 50 mcg ethinyl estradiol for about 5 to about 9 days;
   (c) a composition III containing about 0.3 to about 1.5 mg norethindrone acetate and about 25 to 50 mcg ethinyl estradiol for about 8 to about 12 days; and
   (d) a composition IV that contains ferrous fumarate or is a placebo for 1 to 4 days,
   wherein the sequential administration of compositions I, II, III and IV is repeated and the daily administration of compositions I, II, III and IV is for a 28 day period, wherein composition III contains at least 5 mcg of ethinyl estradiol more than composition II.

10. The method according to claim 9, wherein each of compositions I, II and III contain about 0.5 to about 1.5 mg of norethindrone acetate.

11. A method of contraception comprising the steps of sequentially administering to a female of child bearing age:
   (a) a composition I containing about 1 mg norethindrone acetate and about 5 mcg of ethinyl estradiol for 7 days;
   (b) a composition II containing about 1 mg of norethindrone acetate and about 10 mcg of ethinyl estradiol for 7 days;
   (c) a composition III containing about 1 mg of norethindrone acetate and about 25 mcg of ethinyl estradiol for 10 days; and
   (d) a composition IV which contains ferrous fumarate or is a placebo for 4 days, wherein the sequential administration of compositions I, II, III and IV is repeated upon the completion of the administration of composition IV.

* * * * *

UNITED STATES PATENT AND TRADEMARK OFFICE
CERTIFICATE OF CORRECTION

| | |
|---|---|
| PATENT NO. | : 8,124,595 B2 |
| APPLICATION NO. | : 10/987653 |
| DATED | : February 28, 2012 |
| INVENTOR(S) | : Roger M. Boissonneault |

It is certified that error appears in the above-identified patent and that said Letters Patent is hereby corrected as shown below:

COLUMN 3:

Line 62, "break through" should read --breakthrough--.

COLUMN 5:

Line 4, "preferably" should read --preferable--.

COLUMN 6:

Line 39, "contain" should read --contains--.

Signed and Sealed this
First Day of May, 2012

David J. Kappos
*Director of the United States Patent and Trademark Office*